(12) United States Patent
Gupta

(10) Patent No.: US 12,017,011 B2
(45) Date of Patent: Jun. 25, 2024

(54) INTRAVENOUS CATHETER DEVICE

(71) Applicant: Neeraj Gupta, Gurgaon (IN)

(72) Inventor: Neeraj Gupta, Gurgaon (IN)

(73) Assignee: MedSource International LLC, Chaska, MN (US)

( * ) Notice: Subject to any disclaimer, the term of this patent is extended or adjusted under 35 U.S.C. 154(b) by 194 days.

(21) Appl. No.: 17/054,654

(22) PCT Filed: Nov. 11, 2019

(86) PCT No.: PCT/IN2019/050832
§ 371 (c)(1),
(2) Date: Nov. 11, 2020

(87) PCT Pub. No.: WO2021/048867
PCT Pub. Date: Mar. 18, 2021

(65) Prior Publication Data
US 2021/0370020 A1 Dec. 2, 2021

(30) Foreign Application Priority Data

Sep. 10, 2019 (IN) .............................. 201911036272

(51) Int. Cl.
*A61M 25/00* (2006.01)
*A61M 25/06* (2006.01)
*A61M 39/24* (2006.01)

(52) U.S. Cl.
CPC .... *A61M 25/0028* (2013.01); *A61M 25/0606* (2013.01); *A61M 25/0693* (2013.01); *A61M 2039/2426* (2013.01)

(58) Field of Classification Search
CPC .......... A61M 25/0693; A61M 25/0028; A61M 25/0606; A61M 2039/2426;
(Continued)

(56) References Cited

U.S. PATENT DOCUMENTS 4,022,191 A 5/1977 Jamshidi
4,269,186 A 5/1981 Loveless et al.
(Continued)

FOREIGN PATENT DOCUMENTS

AU 2002340363 B2 8/2008
CA 2178267 A1 12/1996
(Continued)

OTHER PUBLICATIONS

Zeus, Inc., PTFE, Jul. 4, 2017, Zeus Inc. (Year: 2017).*
(Continued)

*Primary Examiner* — Lauren P Farrar
*Assistant Examiner* — Kathleen Paige Farrell
(74) *Attorney, Agent, or Firm* — Dorsey & Whitney LLP

(57) ABSTRACT

The intravenous catheter device (100) includes a catheter hub (102), a valve member (158), an actuator member (176) and a valve closure member (192). The valve member (158) includes a convex portion (162) provided with slits (170) defining prongs (172). The slits (170) are configured to open when a needle (116) is pierced through the slit (170) to puncture a vein of a patient. The valve closure member (192) is disposed inside the catheter hub (102) such that the first surface (194) of the valve closure member (192) abuts the convex portion (162) of the valve member (158). When the luer lock member (206) abutting the actuator member (176) inside the catheter hub (102) is disengaged, the valve closure member (192) is adapted to push the prongs (172), closing the passage (204) for the fluid flow and preventing blood flow from the punctured vein of the patient.

15 Claims, 11 Drawing Sheets

(58) Field of Classification Search
CPC ...... A61M 2039/064; A61M 2039/062; A61M 39/0693; A61M 25/0618; A61M 25/0097; A61M 39/0606; A61M 5/3275; A61M 2039/0666; A61M 2039/2433; A61M 2039/2446; A61M 39/22

See application file for complete search history.

(56) References Cited

U.S. PATENT DOCUMENTS

| | | | |
|---|---|---|---|
| 4,747,831 A | 5/1988 | Kulli | |
| 4,762,516 A | 8/1988 | Luther et al. | |
| 4,778,453 A | 10/1988 | Lopez | |
| 4,832,696 A | 5/1989 | Luther et al. | |
| 4,834,718 A | 5/1989 | Mcdonald | |
| 4,846,805 A | 6/1989 | Sitar | |
| 4,878,902 A | 11/1989 | Wanderer | |
| 4,887,998 A | 12/1989 | Martin et al. | |
| 4,897,083 A | 1/1990 | Martell | |
| 4,917,668 A | 4/1990 | Haindl | |
| 4,929,241 A | 5/1990 | Kulli | |
| 4,932,940 A | 6/1990 | Walker et al. | |
| 4,944,725 A | 7/1990 | Mcdonald | |
| 4,944,728 A | 7/1990 | Carrell et al. | |
| 4,950,252 A | 8/1990 | Luther et al. | |
| 4,952,207 A | 8/1990 | Lemieux | |
| 4,964,854 A | 10/1990 | Luther | |
| 5,000,740 A | 3/1991 | Ducharme et al. | |
| 5,002,536 A | 3/1991 | Thompson et al. | |
| 5,013,304 A | 5/1991 | Russell et al. | |
| 5,030,205 A | 7/1991 | Holdaway et al. | |
| 5,078,694 A | 1/1992 | Wallace | |
| 5,092,845 A | 3/1992 | Chang | |
| 5,098,410 A | 3/1992 | Kerby et al. | |
| 5,108,379 A | 4/1992 | Dolgin et al. | |
| 5,120,319 A | 6/1992 | Van Heugten | |
| 5,135,504 A | 8/1992 | Mclees | |
| 5,156,599 A | 10/1992 | Ranford et al. | |
| 5,195,974 A | 3/1993 | Hardy | |
| 5,195,992 A | 3/1993 | Dudar et al. | |
| 5,205,829 A | 4/1993 | Lituchy | |
| 5,215,525 A | 6/1993 | Sturman | |
| 5,215,528 A | 6/1993 | Purdy et al. | |
| RE34,416 E | 10/1993 | Lemieux | |
| 5,300,045 A | 4/1994 | Plassche, Jr. | |
| 5,322,517 A | 6/1994 | Sircom et al. | |
| 5,328,482 A | 7/1994 | Sircom et al. | |
| 5,334,158 A | 8/1994 | Mclees | |
| 5,344,408 A | 9/1994 | Partika | |
| 5,409,461 A | 4/1995 | Steinman | |
| 5,423,766 A | 6/1995 | Di | |
| 5,533,974 A | 7/1996 | Gaba | |
| 5,558,651 A | 9/1996 | Crawford et al. | |
| 5,562,631 A | 10/1996 | Bogart | |
| 5,599,310 A | 2/1997 | Bogert | |
| 5,601,532 A | 2/1997 | Gaba | |
| 5,601,535 A | 2/1997 | Byrne et al. | |
| 5,601,536 A | 2/1997 | Crawford et al. | |
| 5,611,781 A | 3/1997 | Sircom et al. | |
| 5,662,610 A | 9/1997 | Sircom | |
| 5,676,658 A | 10/1997 | Erskine | |
| 5,688,249 A | 11/1997 | Chang et al. | |
| 5,690,619 A | 11/1997 | Erskine | |
| 5,695,474 A | 12/1997 | Daugherty | |
| 5,697,907 A | 12/1997 | Gaba | |
| 5,702,367 A | 12/1997 | Cover et al. | |
| 5,713,876 A | 2/1998 | Bogert et al. | |
| 5,810,785 A | 9/1998 | Bogert et al. | |
| 5,830,189 A | 11/1998 | Chang | |
| 5,853,393 A | 12/1998 | Bogert | |
| 5,879,337 A | 3/1999 | Kuracina et al. | |
| 5,911,705 A | 6/1999 | Howell | |
| 6,004,294 A | 12/1999 | Brimhall et al. | |
| 6,050,976 A | 4/2000 | Thorne et al. | |
| 6,077,244 A | 6/2000 | Botich et al. | |
| 6,117,108 A | 9/2000 | Woehr et al. | |
| 6,203,527 B1 | 3/2001 | Zadini et al. | |
| 6,221,047 B1 | 4/2001 | Greene et al. | |
| 6,280,419 B1 | 8/2001 | Vojtasek | |
| 6,287,278 B1 | 9/2001 | Woehr et al. | |
| 6,287,317 B1 | 9/2001 | Makower et al. | |
| 6,379,337 B1 | 4/2002 | Mohammad M. B. B. S. | |
| 6,461,362 B1 | 10/2002 | Halseth et al. | |
| 6,491,707 B2 | 12/2002 | Makower et al. | |
| 6,533,759 B1 | 3/2003 | Watson et al. | |
| 6,582,402 B1 | 6/2003 | Erskine | |
| 6,595,954 B1 | 7/2003 | Luther et al. | |
| 6,595,955 B2 | 7/2003 | Ferguson et al. | |
| 6,616,630 B1 | 9/2003 | Woehr et al. | |
| 6,620,136 B1 | 9/2003 | Pressly, Sr. et al. | |
| 6,623,458 B2 | 9/2003 | Woehr et al. | |
| 6,629,957 B1 | 10/2003 | Wiklund | |
| 6,629,959 B2 | 10/2003 | Kuracina et al. | |
| 6,652,490 B2 | 11/2003 | Howell | |
| 6,689,102 B2 | 2/2004 | Greene | |
| D491,266 S | 6/2004 | Cindrich et al. | |
| 6,796,962 B2 | 9/2004 | Ferguson et al. | |
| 6,860,871 B2 | 3/2005 | Kuracina et al. | |
| 6,872,193 B2 | 3/2005 | Shaw et al. | |
| 6,893,423 B2 | 5/2005 | Denolly | |
| 6,902,546 B2 | 6/2005 | Ferguson | |
| 6,942,652 B1 | 9/2005 | Pressly, Sr. et al. | |
| 6,972,002 B2 | 12/2005 | Thorne | |
| 6,979,333 B2 | 12/2005 | Hammerslag | |
| 6,981,965 B2 | 1/2006 | Luther et al. | |
| 6,995,814 B2 | 2/2006 | Kanatsu | |
| 7,014,622 B1 | 3/2006 | Pressly, Sr. et al. | |
| 7,037,292 B2 | 5/2006 | Carlyon et al. | |
| 7,179,244 B2 | 2/2007 | Smith et al. | |
| 7,186,239 B2 | 3/2007 | Woehr | |
| 7,255,685 B2 | 8/2007 | Pressly, Sr. et al. | |
| 7,264,613 B2 | 9/2007 | Woehr et al. | |
| 7,303,547 B2 | 12/2007 | Pressly, Sr. et al. | |
| 7,341,573 B2 | 3/2008 | Ferguson et al. | |
| 7,344,516 B2 | 3/2008 | Erskine | |
| 7,347,853 B2 | 3/2008 | Difiore et al. | |
| 7,413,562 B2 | 8/2008 | Ferguson et al. | |
| 7,500,965 B2 | 3/2009 | Menzi et al. | |
| D592,302 S | 5/2009 | Stokes et al. | |
| 7,534,227 B2 | 5/2009 | Kulli | |
| 7,604,616 B2 | 10/2009 | Thoresen et al. | |
| 7,611,499 B2 | 11/2009 | Woehr et al. | |
| 7,625,360 B2 | 12/2009 | Woehr et al. | |
| 7,632,243 B2 | 12/2009 | Bialecki et al. | |
| 7,658,725 B2 | 2/2010 | Bialecki et al. | |
| 7,678,080 B2 | 3/2010 | Shue et al. | |
| 7,699,807 B2 | 4/2010 | Faust et al. | |
| 7,736,342 B2 | 6/2010 | Abriles et al. | |
| 7,753,877 B2 | 7/2010 | Bialecki et al. | |
| 7,753,887 B2 | 7/2010 | Botich et al. | |
| 7,785,296 B2 | 8/2010 | Muskatello et al. | |
| 7,828,774 B2 | 11/2010 | Harding et al. | |
| 7,951,121 B2 | 5/2011 | Weaver et al. | |
| 7,963,948 B2 | 6/2011 | Melsheimer | |
| 7,972,313 B2 | 7/2011 | Woehr et al. | |
| 8,062,252 B2 | 11/2011 | Alheidt et al. | |
| 8,070,725 B2 | 12/2011 | Christensen | |
| 8,105,288 B2 | 1/2012 | Keyser et al. | |
| 8,133,206 B2 | 3/2012 | Greene et al. | |
| 8,172,805 B2 | 5/2012 | Mogensen et al. | |
| 8,211,070 B2 | 7/2012 | Woehr et al. | |
| 8,235,946 B2 | 8/2012 | Molgaard-Nielsen | |
| 8,251,950 B2 | 8/2012 | Albert et al. | |
| 8,257,322 B2 | 9/2012 | Koehler et al. | |
| 8,282,605 B2 | 10/2012 | Tan et al. | |
| 8,308,685 B2 | 11/2012 | Botich et al. | |
| 8,308,691 B2 | 11/2012 | Woehr et al. | |
| 8,328,762 B2 | 12/2012 | Woehr et al. | |
| 8,333,735 B2 | 12/2012 | Woehr et al. | |
| 8,337,463 B2 | 12/2012 | Woehr et al. | |
| 8,377,040 B2 | 2/2013 | Burkholz et al. | |
| 8,382,721 B2 | 2/2013 | Woehr et al. | |
| 8,398,597 B2 | 3/2013 | Brimhall | |
| 8,403,886 B2 | 3/2013 | Bialecki et al. | |
| 8,454,574 B2 | 6/2013 | Weaver et al. | |

(56) References Cited

U.S. PATENT DOCUMENTS

| | | | |
|---|---|---|---|
| 8,454,579 B2* | 6/2013 | Fangrow, Jr. | A61M 39/22 604/539 |
| 8,460,247 B2 | 6/2013 | Woehr et al. | |
| 8,540,728 B2 | 9/2013 | Woehr et al. | |
| 8,568,372 B2 | 10/2013 | Woehr et al. | |
| 8,585,660 B2 | 11/2013 | Murphy | |
| 8,591,469 B2 | 11/2013 | Keyser et al. | |
| 8,597,249 B2 | 12/2013 | Woehr et al. | |
| 8,603,009 B2 | 12/2013 | Tan et al. | |
| 8,647,301 B2 | 2/2014 | Bialecki et al. | |
| 8,647,313 B2 | 2/2014 | Woehr et al. | |
| 8,771,230 B2 | 7/2014 | White et al. | |
| 8,784,386 B2 | 7/2014 | Baid | |
| 8,795,198 B2 | 8/2014 | Tan et al. | |
| 8,814,833 B2 | 8/2014 | Farrell et al. | |
| D713,522 S | 9/2014 | Woehr et al. | |
| D713,957 S | 9/2014 | Woehr et al. | |
| 8,827,965 B2 | 9/2014 | Woehr et al. | |
| 8,834,422 B2 | 9/2014 | Walker et al. | |
| 8,845,584 B2 | 9/2014 | Ferguson et al. | |
| 8,882,742 B2 | 11/2014 | Dikeman et al. | |
| 8,936,575 B2 | 1/2015 | Moulton | |
| 9,033,927 B2 | 5/2015 | Maan et al. | |
| 9,095,683 B2 | 8/2015 | Hall et al. | |
| 9,149,626 B2 | 10/2015 | Woehr et al. | |
| 9,174,036 B2 | 11/2015 | Okamura et al. | |
| 9,186,455 B2 | 11/2015 | Moyer | |
| 9,278,195 B2 | 3/2016 | Erskine | |
| 9,289,237 B2 | 3/2016 | Woehr et al. | |
| 9,314,608 B2 | 4/2016 | Weaver et al. | |
| 9,320,870 B2 | 4/2016 | Woehr | |
| 9,370,641 B2 | 6/2016 | Woehr et al. | |
| 9,402,964 B2 | 8/2016 | Crawford | |
| 9,427,549 B2 | 8/2016 | Woehr et al. | |
| 9,504,786 B2 | 11/2016 | Carlyon et al. | |
| 9,555,220 B2 | 1/2017 | Koehler et al. | |
| 9,555,221 B2 | 1/2017 | Koehler et al. | |
| 9,604,035 B2 | 3/2017 | Keyser et al. | |
| 9,623,210 B2 | 4/2017 | Woehr | |
| 9,764,085 B2 | 9/2017 | Teoh | |
| 9,775,972 B2 | 10/2017 | Christensen et al. | |
| 9,775,973 B2 | 10/2017 | Keyser et al. | |
| 9,782,546 B2 | 10/2017 | Woehr | |
| 9,827,398 B2 | 11/2017 | White et al. | |
| 9,844,646 B2 | 12/2017 | Knutsson | |
| 9,844,648 B2 | 12/2017 | Nakajima et al. | |
| 9,933,079 B2 | 4/2018 | Weaver et al. | |
| 9,962,525 B2 | 5/2018 | Woehr | |
| 10,028,691 B2 | 7/2018 | Goral et al. | |
| 10,052,474 B2 | 8/2018 | Keyser et al. | |
| 10,080,869 B2 | 9/2018 | Woehr et al. | |
| 10,307,571 B2 | 6/2019 | Burkholz | |
| 10,314,984 B2 | 6/2019 | Koehler et al. | |
| 10,406,327 B2 | 9/2019 | Holm et al. | |
| 10,449,331 B2 | 10/2019 | Lim et al. | |
| 10,456,572 B2 | 10/2019 | Woehr | |
| 10,500,375 B2 | 12/2019 | Isaacson et al. | |
| 10,500,376 B2 | 12/2019 | Isaacson et al. | |
| 10,548,522 B2 | 2/2020 | Akcay et al. | |
| 10,589,081 B2 | 3/2020 | Servin De La Mora Godinez et al. | |
| 10,596,351 B2 | 3/2020 | Liska | |
| 10,625,067 B2 | 4/2020 | Al-ali | |
| 10,661,058 B2 | 5/2020 | Woehr | |
| 10,675,440 B2 | 6/2020 | Abitabilo et al. | |
| 10,682,499 B2 | 6/2020 | Isaacson et al. | |
| 10,695,551 B2 | 6/2020 | Shevgoor et al. | |
| 10,835,729 B2 | 11/2020 | Agrawal et al. | |
| 10,850,068 B2 | 12/2020 | Teoh | |
| 11,071,849 B2 | 7/2021 | Ng et al. | |
| 2002/0161386 A1 | 10/2002 | Halseth et al. | |
| 2002/0169418 A1 | 11/2002 | Menzi et al. | |
| 2003/0060760 A1 | 3/2003 | Botich et al. | |
| 2003/0083620 A1 | 5/2003 | Luther et al. | |
| 2003/0100868 A1 | 5/2003 | Ferguson et al. | |
| 2003/0199827 A1 | 10/2003 | Thorne | |
| 2004/0049155 A1 | 3/2004 | Schramm | |
| 2004/0059296 A1 | 3/2004 | Godfrey | |
| 2004/0078003 A1 | 4/2004 | Smith et al. | |
| 2004/0127854 A1 | 7/2004 | Leinsing et al. | |
| 2004/0158208 A1 | 8/2004 | Hiejima | |
| 2004/0168690 A1 | 9/2004 | Payne | |
| 2004/0186434 A1 | 9/2004 | Harding et al. | |
| 2004/0204681 A1 | 10/2004 | Thoresen et al. | |
| 2004/0236288 A1 | 11/2004 | Howell et al. | |
| 2004/0267204 A1 | 12/2004 | Brustowicz | |
| 2005/0038384 A1 | 2/2005 | Li | |
| 2005/0096592 A1 | 5/2005 | Carlyon et al. | |
| 2005/0113755 A1 | 5/2005 | Greene et al. | |
| 2005/0277879 A1 | 12/2005 | Daga | |
| 2006/0036219 A1 | 2/2006 | Alvin | |
| 2006/0041231 A1 | 2/2006 | Pressly et al. | |
| 2006/0229556 A1 | 10/2006 | Pressly et al. | |
| 2007/0191776 A1 | 8/2007 | Bialecki et al. | |
| 2008/0097330 A1 | 4/2008 | King et al. | |
| 2008/0119795 A1 | 5/2008 | Erskine | |
| 2008/0228150 A1 | 9/2008 | Jones et al. | |
| 2009/0137958 A1 | 5/2009 | Erskine | |
| 2009/0209912 A1 | 8/2009 | Keyser et al. | |
| 2009/0222003 A1 | 9/2009 | Otley | |
| 2010/0042048 A1 | 2/2010 | Christensen | |
| 2010/0241087 A1 | 9/2010 | Moulton | |
| 2011/0015573 A1 | 1/2011 | Maan et al. | |
| 2011/0301551 A1 | 12/2011 | Koehler et al. | |
| 2011/0306933 A1 | 12/2011 | Djordejevic et al. | |
| 2011/0319825 A1 | 12/2011 | Goral et al. | |
| 2012/0035552 A1 | 2/2012 | Woehr | |
| 2012/0089101 A1* | 4/2012 | Carlyon | A61M 25/0606 604/246 |
| 2012/0150118 A1 | 6/2012 | Keyser et al. | |
| 2013/0030391 A1 | 1/2013 | Baid | |
| 2013/0165868 A1* | 6/2013 | Isaacson | A61M 25/0693 29/428 |
| 2013/0237928 A1 | 9/2013 | Fisher et al. | |
| 2014/0025009 A1 | 1/2014 | Erskine | |
| 2014/0052022 A1 | 2/2014 | Tan et al. | |
| 2014/0058357 A1 | 2/2014 | Keyser et al. | |
| 2014/0200549 A1 | 7/2014 | Norkunas | |
| 2014/0236099 A1 | 8/2014 | Nakagami et al. | |
| 2014/0336582 A1 | 11/2014 | Tisci | |
| 2014/0365809 A1 | 12/2014 | Higeta et al. | |
| 2014/0371715 A1 | 12/2014 | Farrell et al. | |
| 2015/0094751 A1 | 4/2015 | Chen et al. | |
| 2015/0224267 A1 | 8/2015 | Farrell et al. | |
| 2015/0265827 A1 | 9/2015 | Keyser et al. | |
| 2015/0328438 A1 | 11/2015 | Baid | |
| 2016/0008581 A1 | 1/2016 | Ang et al. | |
| 2016/0175563 A1 | 6/2016 | Woehr et al. | |
| 2016/0175576 A1* | 6/2016 | Neff et al. | A61M 39/0613 |
| 2016/0220161 A1 | 8/2016 | Goral et al. | |
| 2016/0220791 A1 | 8/2016 | Akcay et al. | |
| 2016/0271370 A1 | 9/2016 | Keyser et al. | |
| 2016/0331935 A1* | 11/2016 | Saatchi | A61M 25/0662 |
| 2016/0361490 A1 | 12/2016 | Phang et al. | |
| 2016/0361519 A1* | 12/2016 | Teoh | A61M 25/0606 |
| 2016/0374685 A1 | 12/2016 | Abbott et al. | |
| 2017/0035992 A1 | 2/2017 | Harding et al. | |
| 2017/0035995 A1 | 2/2017 | Shevgoor et al. | |
| 2017/0043134 A1 | 2/2017 | Harding et al. | |
| 2017/0120011 A1 | 5/2017 | Burkholz et al. | |
| 2017/0120017 A1 | 5/2017 | Burkholz et al. | |
| 2017/0274183 A1 | 9/2017 | Burkholz et al. | |
| 2017/0319822 A1 | 11/2017 | Ang | |
| 2017/0333642 A1 | 11/2017 | Shevgoor et al. | |
| 2017/0361070 A1 | 12/2017 | Hivert | |
| 2018/0064912 A1 | 3/2018 | Keyser et al. | |
| 2018/0078741 A1 | 3/2018 | Stokes | |
| 2018/0154119 A1 | 6/2018 | White et al. | |
| 2018/0214673 A1* | 8/2018 | Ng et al. | A61M 25/0606 |
| 2018/0214682 A1 | 8/2018 | Woehr et al. | |
| 2018/0256885 A1 | 9/2018 | Shevgoor et al. | |
| 2018/0289932 A1 | 10/2018 | Isaacson et al. | |
| 2018/0296149 A1 | 10/2018 | Goral et al. | |
| 2018/0304048 A1 | 10/2018 | Knutsson | |

(56) References Cited

U.S. PATENT DOCUMENTS

| | | | |
|---|---|---|---|
| 2018/0311475 | A1 | 11/2018 | Baid |
| 2018/0361119 | A1 | 12/2018 | Goral et al. |
| 2019/0160264 | A1 | 5/2019 | Isaacson |
| 2019/0262549 | A1 | 8/2019 | Koehler et al. |
| 2019/0351210 | A1 | 11/2019 | Solomon et al. |
| 2020/0094026 | A1 | 3/2020 | Isaacson et al. |
| 2020/0094037 | A1 | 3/2020 | Tran et al. |
| 2020/0121896 | A1 | 4/2020 | Baid |
| 2020/0146605 | A1 | 5/2020 | Paliwoda |
| 2020/0188634 | A1 | 6/2020 | Woehr et al. |
| 2020/0197667 | A1 | 6/2020 | Gupta |
| 2020/0261702 | A1 | 8/2020 | Jewell et al. |
| 2021/0308427 | A1 | 10/2021 | Ng et al. |
| 2021/0402143 | A1 | 12/2021 | Yokota et al. |

FOREIGN PATENT DOCUMENTS

| | | |
|---|---|---|
| CA | 2033361 C | 11/2002 |
| CA | 2710969 A1 | 7/2009 |
| CN | 106659438 A | 5/2017 |
| CN | 107427633 A | 12/2017 |
| DE | 4442352 C1 | 12/1995 |
| EP | 0747083 A2 | 12/1996 |
| EP | 0747085 A2 | 12/1996 |
| EP | 0750916 A2 | 1/1997 |
| EP | 3209363 B1 | 3/2019 |
| EP | 3622999 A1 | 3/2020 |
| IN | 201911036272 | 1/2020 |
| JP | 07024071 A | 1/1995 |
| JP | 2001046507 A | 2/2001 |
| JP | 2001190683 A | 7/2001 |
| JP | 20041544364 A | 6/2004 |
| WO | 9308865 | 5/1993 |
| WO | 9413341 | 6/1994 |
| WO | 0168174 A2 | 9/2001 |
| WO | 2007061718 A2 | 5/2007 |
| WO | 2007098355 A1 | 8/2007 |
| WO | 2010107645 A1 | 9/2010 |
| WO | 2011152916 A1 | 12/2011 |
| WO | 2013051242 A1 | 4/2013 |
| WO | 2016033143 A1 | 3/2016 |
| WO | 2016063287 A1 | 4/2016 |
| WO | 2016135293 A2 | 9/2016 |
| WO | 2017042825 A2 | 3/2017 |
| WO | 2018096549 A1 | 5/2018 |
| WO | 2018217781 A1 | 11/2018 |
| WO | 2019008432 A1 | 1/2019 |
| WO | 2019152630 A1 | 8/2019 |
| WO | 2020011663 A1 | 1/2020 |
| WO | 2020120404 A1 | 6/2020 |
| WO | 2020189466 A1 | 9/2020 |
| WO | 2021048867 A1 | 3/2021 |

OTHER PUBLICATIONS

International Search Report and Written Opinion dated Apr. 19, 2022 in connection with International Patent Application No. PCT/US2022/016002, 7 pages.

International Search Report and Written Opinion for PCT Application No. PCT/IN2018/050178, dated Jun. 12, 2018, 8 pages.

International Search Report and Written Opinion dated Jul. 20, 2022 in connection with International Patent Application No. PCT/US2022/027597, 9 pages.

International Search Report and Written Opinion issued in International Application No. PCT/US2023/060554, dated May 9, 2023, 11 pages.

International Search Report and Written Opinion issued in International Application No. PCT/US2023/060560, dated Jun. 2, 2023, 10 pages.

Murty, "Use of Stainless Steels in Medical Applications", Medical Device Materials: Proceedings of the Material & Processes for Medical Devices Conference, pp. 288, 2003.

International Preliminary Report on Patentability issued in International Application No. PCT/US2022/016002, dated Aug. 24, 2023, 6 pages.

* cited by examiner

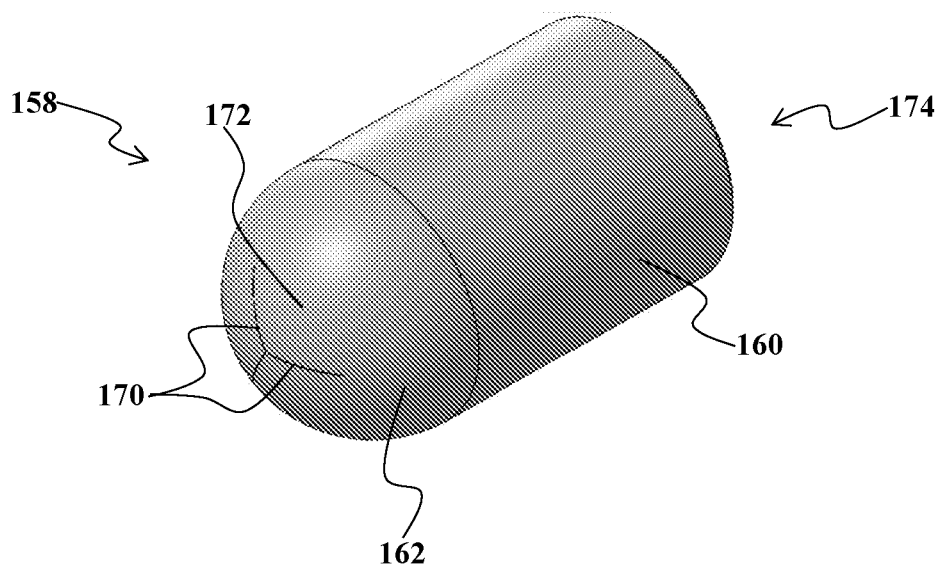
FIG. 6a
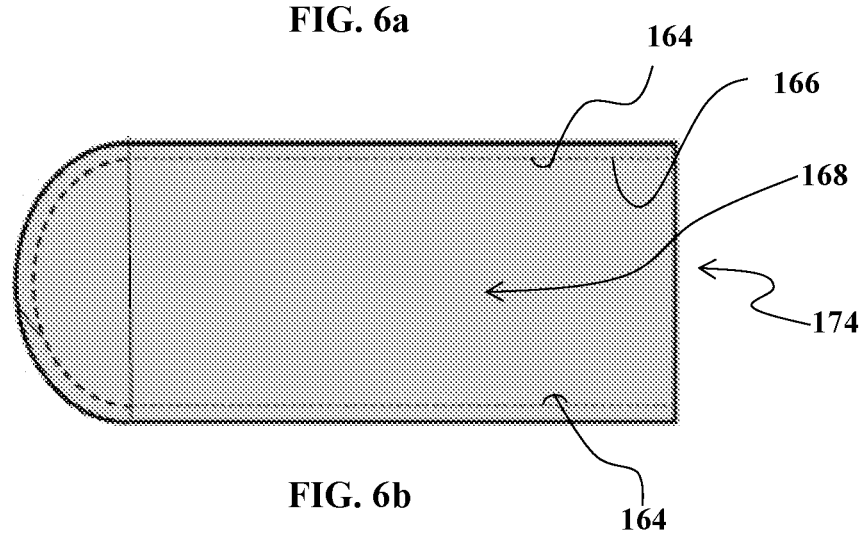
FIG. 6b
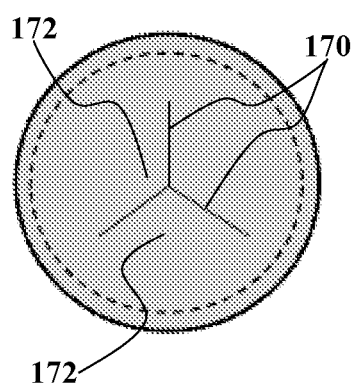 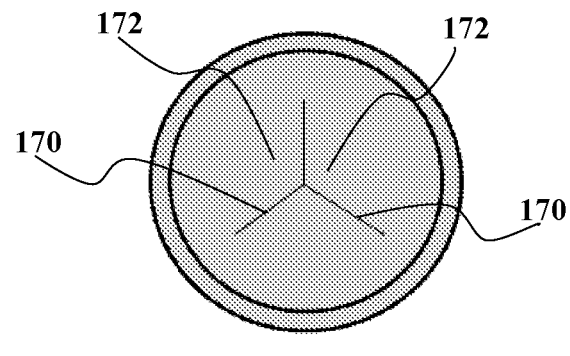
FIG. 6c　　　　　　　　FIG. 6d

INTRAVENOUS CATHETER DEVICE

CROSS-REFERENCE TO RELATED APPLICATIONS

This application is a U.S. National Stage Application of International Patent Application No. PCT/IN2019/050832, filed Nov. 11, 2019, entitled "An Intravenous Catheter Device", which claims priority to Indian Patent Application No. 201911036272, filed Sep. 10, 2019, entitled "An Intravenous Catheter Device", each of which is incorporated by reference herein, in the entirety and for all purposes.

TECHNICAL FIELD

Present disclosure relates to a medical device. More particularly it relates to an intravenous catheter device to prevent backflow of blood.

BACKGROUND OF THE DISCLOSURE AND PRIOR ARTS

Catheters have been used by mankind since ancient times. Ancient Syrians made catheters out of reeds. Ancient Greeks used hollow metal tubes which are inserted through a urethra into a urinary bladder of a patient to empty the urinary bladder. In modern medicine, catheter use was first described by Dr. N. B. Sornborger who patented syringe and catheter in 1868.

Intravenous (IV) catheters have also been in existence since many years. Intravenous catheters are venous devices used to infuse medication or fluids directly into a vein or draw blood samples for testing. Intravenous catheters are introduced into a vein using a needle and fixed to the patient's skin with an adhesive tape.

One drawback associated with the use of over-needle intravenous catheters is that once the needle is withdrawn from the catheter, there is an open channel for the blood to flow through the catheter and spill out of the catheter hub. The blood may be contaminated and this may lead to risk of infection for the healthcare worker. Additionally, spillage of blood leads to unhygienic conditions for the patient as well as in the healthcare space where the catheter is applied and blood spillage is currently a major problem during administration of IV catheter.

There are known methods to avoid blood spillage, but these methods include certain risks and drawbacks associated with each of the methods, where a manual pressure is applied on the vein before withdrawal of needle to stop the flow of blood but this method requires either two hand technique with correct skill or two operators may be required, still the flow of blood cannot be stopped. A closed system intravenous catheter is used in which the flow of blood is stopped by having a dead stopper in the path of the blood flow and a side port is provided at an angle to the catheter in order allow air escape for flashback visualization and to allow infusion of fluid. However, these products are bulky, complicated to use and more expensive than standard products.

In another known method, the catheter space may be blocked by a mandrel or obturator which requires proper skill and training and that further makes the product complicated in structure and to operate, and expensive.

Another known catheter device is disclosed in the U.S. Pat. No. 4,874,377 (hereinafter referred to as the Pat '377). The Pat '377 describes a catheter hub assembly with a valve to prevent the back flow of blood. The valve deforms with pressure when a connector is attached to the catheter hub and the deformation is controlled in a way that allows fluid to pass. It is assumed that in order to allow for the deformation in the Pat '377, the diameter and overall size of the hub would be increased. Though the Pat '377 attempts to provide a practically possible solution, the increase in size interferes substantially with the overall functioning of the product and greatly impacts patient comfort.

Yet another known catheter device is disclosed in the U.S. Pat. No. 5,064,416 (hereinafter referred to as the Pat '416). The Pat '416 describes a frusto-conical actuator with a smooth tip that is activated with a luer connection but slips back when the connection is removed. This type of movement is fraught with practical problems especially for devices where the shelf life is long (e.g. 3 years or more). Further the Pat '416 does not describe as to how the valve is designed or fitted into the catheter hub.

Yet another known catheter device is disclosed in the U.S. Pat. No. 5,154,703 (hereinafter referred to as the Pat '703). The Pat '703 describes a simple disc shaped valve combined with a sharp needle that pierces this disc on connection with a luer. The addition of a sharp needle in the Pat '703 brings many safety-related issues including proper handling and disposal of the product. Assembling a sharp needle of a small size within a small assembly is also complicated.

Yet another known catheter device is disclosed in the U.S. Pat. No. 5,053,014 (hereinafter referred to as the Pat '014). The Pat '014 describes a two-part catheter hub assembly into which a membrane is inserted using an interference fit. A smooth plunger is then also enclosed within the part assembly so that it penetrates the membrane when a luer connection is applied.

Yet another kind of catheter device disclosed in the PCT patent publication number WO2017042825A2 (hereinafter referred to as the patent '825). The catheter device in the patent '825 discloses one-way valve having slits for preventing reverse flow of the blood when a vein is punctured by a needle.

Yet another kind of catheter device disclosed in the PCT patent publication number WO2018096549A1 (hereinafter referred to as the patent '549). The catheter device in the patent '549 discloses one-way valve having slits for preventing reverse flow of the blood when the vein if punctures by a needle.

However, the slits in the one-way valve in the patents '825 and '549 do not close fully when the user wants to close the fluid path and the one-way valves do not provide the complete solution that was intended to do.

Although many designs of valve with or without an actuator are provided for prevention of back flow of blood, but the designs of these valve are very complex and include considerable challenges in manufacturing, assembly and product performance.

Therefore, the present disclosure is directed to overcome one or more of the problems as set forth above.

SUMMARY OF THE DISCLOSURE

One object of present disclosure is to provide an intravenous catheter to avoid reverse flow of blood.

Another object of present disclosure is to provide an intravenous catheter with a novel one-way valve design which is responsible for prevention of reverse flow of blood.

Another object of present disclosure is to provide a mechanism for preventing reverse flow of blood that may be applied to a variety of other catheter devices.

The present invention is related to an intravenous catheter device. The intravenous catheter device comprises a catheter hub having a proximal end and a distal end, a co-axial recess with an annular stopper disposed at the proximal end of the catheter hub, and an undercut portion provided towards the distal end of the catheter hub. The intravenous catheter device further includes a valve member which is adapted to be disposed inside the co-axial recess of the catheter hub. The valve member is defined by a cylindrical portion and a curved portion disposed at one end of the cylindrical portion, a co-axial recess extending from the cylindrical portion to the curved portion. The curved portion is being provided with one or more slits defining a plurality of prongs. The slits are configured to allow a needle to pass through the slits to puncture a vein of a patient. The intravenous catheter device further includes a flashback chamber adapted to be disposed at the proximal end of the catheter hub, wherein a blood flow into the flashback chamber confirms puncturing of the vein by the needle. The intravenous catheter device further includes an actuator member having an axial bore. The actuator member is adapted to be disposed within the co-axial recess of the valve member. The actuator member is displaced axially in a direction towards the distal end of the catheter hub thereby opening the plurality of prongs of the valve member to form a passage for a fluid flow from the proximal end of the catheter hub to the distal end of the catheter hub, when a luer lock member is removably connected at the proximal end of catheter hub abutting the actuator member. The intravenous catheter device further includes a valve closure member comprising a first surface at a proximal end, a second surface at a distal end and a through hole extending between the proximal end and the distal end, the valve closure member is disposed inside the catheter hub such that the first surface of the valve closure member abuts the undercut portion of the catheter hub and the second surface of the valve closure member abuts the curved portion of the valve member, wherein the valve closure member is adapted to close the plurality of prongs of the valve member, thereby closing the passage for the fluid flow and preventing blood flow from the punctured vein of the patient from the distal end of the catheter hub to the proximal end of the catheter hub, when the luer lock member abutting the actuator member is removed.

In an embodiment, the valve closure member has hardness ranging from about 50 shore to about 80 shore and the valve member has hardness ranging from about 20 shore to about 45 shore.

In an embodiment, the first surface of the valve closure member is in concave shape or a frusto-conical shaped in a cavity form.

In an embodiment, the curved portion of the valve member is in convex shape or a frusto-conical shaped shape.

In an embodiment, the valve member is adapted to be held in place at the co-axial recess of the catheter hub when a first end of the valve member abuts the annular stopper of the catheter hub.

In an embodiment, the valve member is made of a flexible material selected from a group consisting of silicone and rubber.

In an embodiment, the slits are of Y-shape or X-shape or + shape or a combination of the same.

In an embodiment, the cylindrical portion of the valve member has a protrusion at an inner surface.

In an embodiment, the actuator member has a circular recess at an outer surface of the actuator member, and wherein the protrusion of the valve member is adapted to engage with the circular recess of the actuator member, thereby to place an assembly of the valve member and the actuator member intact inside the catheter hub.

In an embodiment, the actuator member includes a first end having a radially extending flange, a second end having a convex surface and the axial bore between the first end and the second end of the actuator member.

In an embodiment, the valve closure member being harder than the hardness of the plurality of prongs of the valve member, when the luer lock member is disengaged from the catheter hub, the valve closure member pushes the plurality of prongs and the actuator member in a direction away from the distal end of the catheter hub thereby closing the passage for the fluid flow and preventing blood flow from the punctured vein of the patient from the distal end of the catheter hub to the proximal end of the catheter hub.

In an embodiment, the actuator member is made of a rigid plastic material or metal.

In an embodiment, the flashback chamber includes any one of a porous filter and a cover to allow air to escape and blood to flow inside the flashback chamber.

In an embodiment, the device includes a needle stick safety device.

BRIEF DESCRIPTION OF ACCOMPANYING DRAWINGS

FIGS. 6a-6d shows a perspective view, a sectional view, a front view, and a rear view of a valve member of the intravenous catheter device shown in FIGS. 1-4, according to an exemplary embodiment of the present disclosure;

DETAILED DESCRIPTION OF THE DISCLOSURE

Provided below is a non-limiting exemplary embodiment of the present disclosure and a reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claim.

Figure 1:
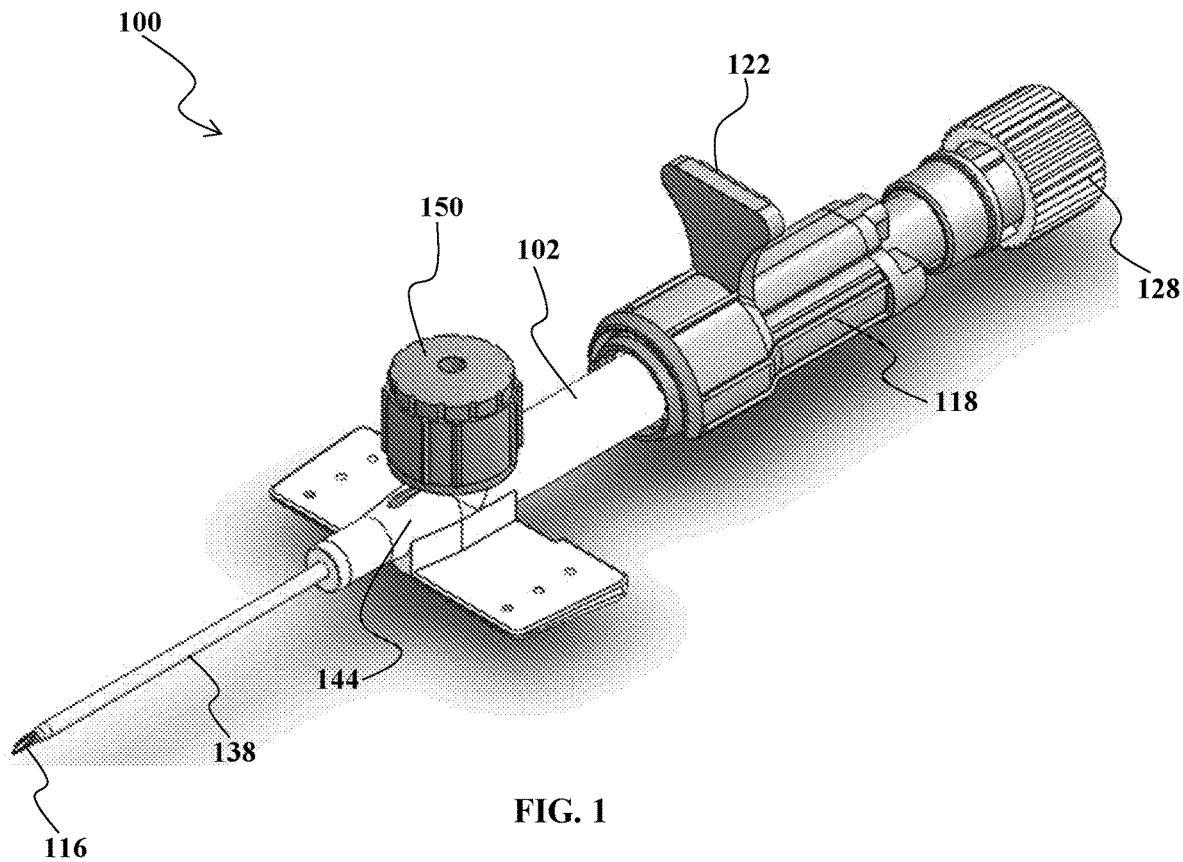
FIG. 1 shows a perspective view of an intravenous catheter device, according to an exemplary embodiment of the present disclosure.
Figure 2:
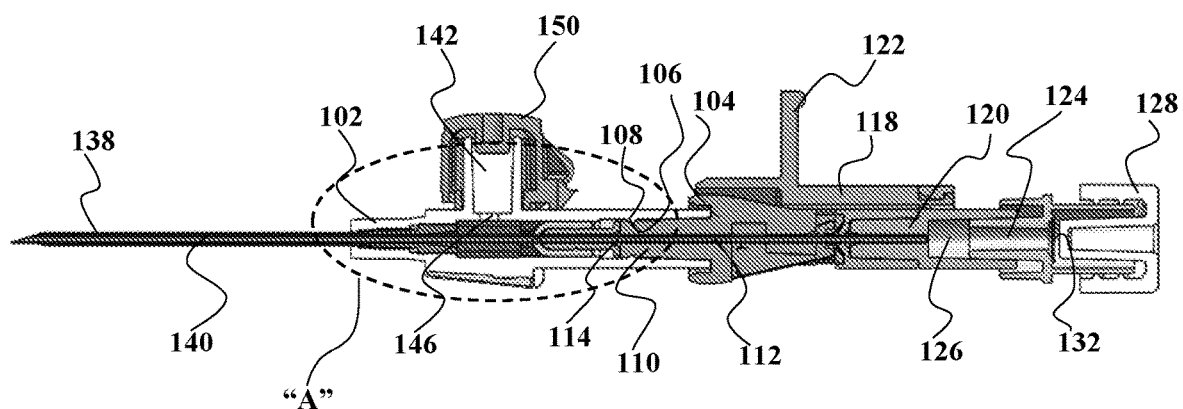
FIG. 2 shows a sectional view of the intravenous catheter device shown in FIG. 1.

FIGS. 1 and 2 illustrate a perspective view and a sectional view of a catheter device (100), respectively, according to an exemplary embodiment of the present disclosure. The catheter device (100) is a medical device used onto patients undergoing a treatment for administration of a medication fluid by an intravenous therapy or the catheter device (100) may be used to carry-out other tasks based on a type of catheter. In the illustrated figures, the catheter device (100) is an intravenous catheter device. The term 'intravenous catheter device' as referred in the present disclosure will be interchangeably used by a term 'catheter device'. It is to be understood that both the terms 'intravenous catheter device' and 'catheter device' relate to same device. The intravenous catheter device (100) as illustrated in the FIG. 1 includes a catheter hub (102) (more clearly shown in FIG. 3, which illustrates a magnified view of the catheter hub (102) and it has been indicated by a portion "A" in FIG. 2).

The catheter device (100) further includes a needle cover (104) which can be connected to the catheter hub (102) in such a way that a recess (106) on the needle cover (104) is engaged with a projection (108) of the catheter hub (102). The needle cover (104) further includes a tubular sleeve (110) with an axially extending slit (112) and a bore (114) for receiving a needle (116), such that when the needle (116) is withdrawn from the catheter hub (102), the needle cover (104) which is in tight fit relationship with the catheter hub (102) disengages the catheter hub (102). In an embodiment, the needle cover (104) of the catheter device (100) includes a safety mechanism or a needle stick safety device (not shown) for preventing exposure of a tip of the needle (116) when the needle (116) is withdrawn from the catheter hub (102) after puncturing a vein (not shown) of a patient. The catheter device (100) further includes a casing (118) which encases both the needle cover (104) and a needle hub (120) in a partial manner. The casing (118) may be provided with a thumb grip (122) for providing a gripping to an operator (not shown) during insertion or retraction of the catheter device (100).

Figure 20A:
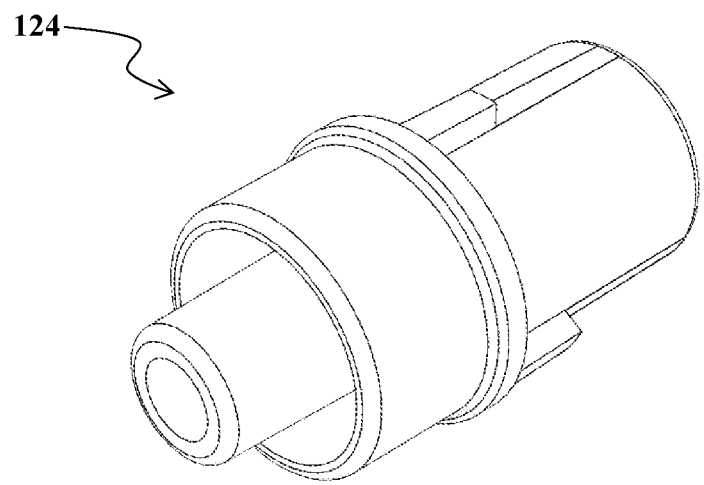
FIGS. 20a and 20b show a perspective view and a sectional view of a flashback chamber having a filter.
Figure 20B:
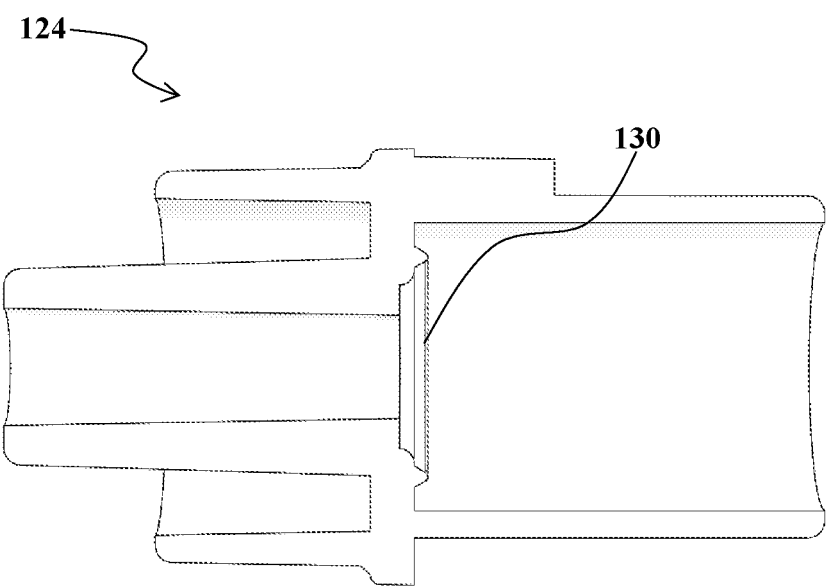

The casing (118) can be detachably connected to the needle cover (104) via ribs (not shown). Further, the needle hub (120) is releasably connected to a flashback chamber (124) through an extended portion (126) of the needle hub (120) and may be closed using a threaded cap or a luer lock cap (128) at one end. The needle hub (120) at the other end is fixedly connected with the needle (116). The blood flow into the flashback chamber (124) confirms puncturing of the vein by the needle (116). The flashback chamber (124) can include any one of a porous filter (130) (shown in FIGS. 20a and 20b) and a cover (not shown) to allow air to escape and blood to flow inside the flashback chamber (124). The flashback chamber (124) may additionally include a hydrophobic filter (132) for preventing spillage of the blood from the flashback chamber (124).

Figure 3:
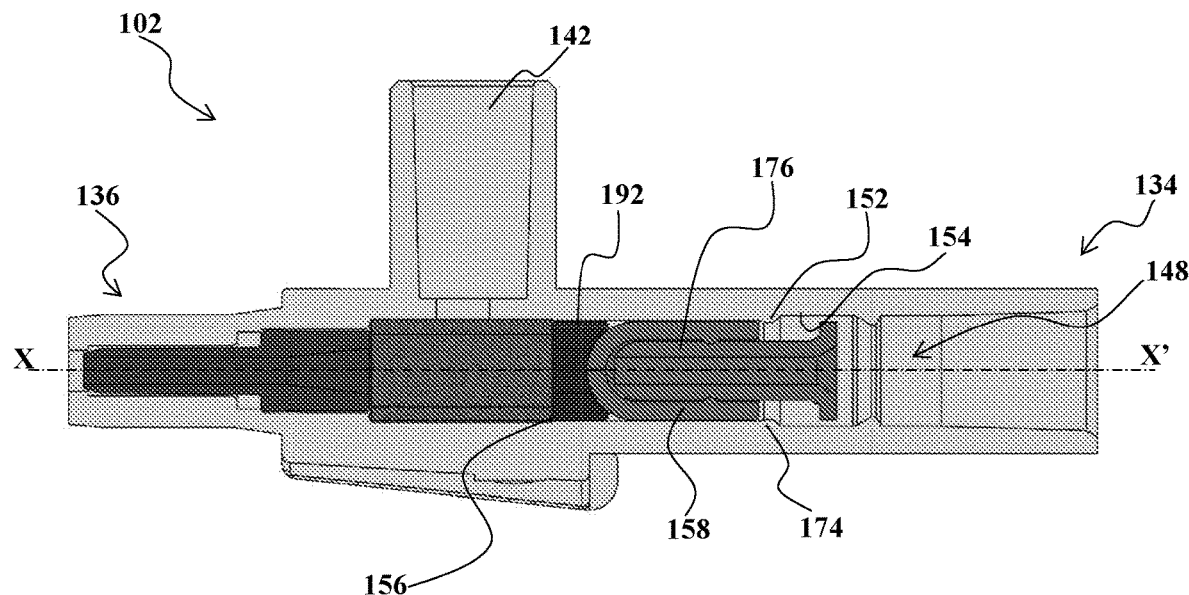
FIG. 3 shows a magnified view of a catheter hub of the intravenous catheter device indicated as a portion "A" indicated in FIG. 2.
Figure 4:
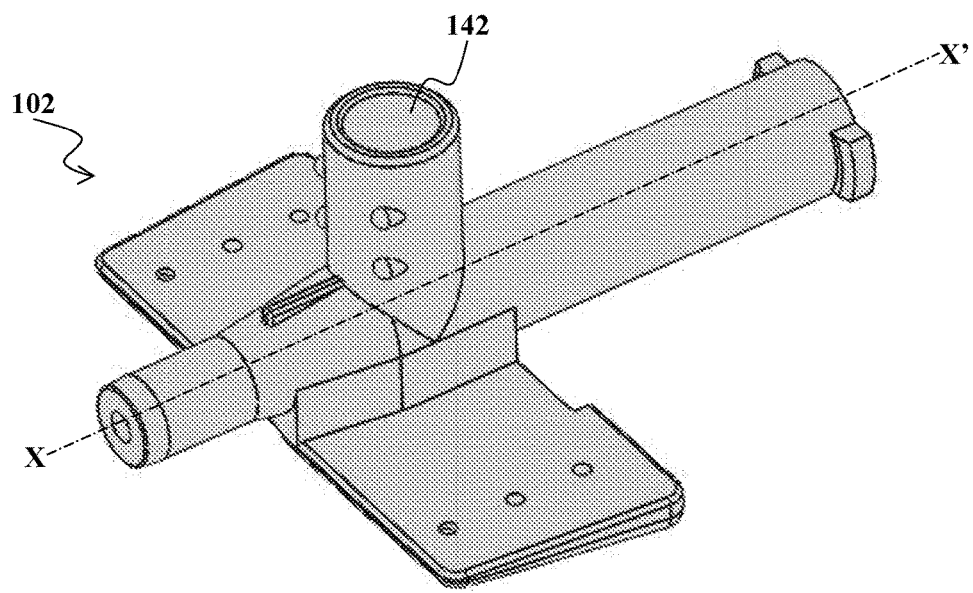
FIG. 4 shows a perspective view of the catheter hub shown in FIGS. 1-3.

FIG. 4 illustrates a perspective view of the catheter hub (102) shown in FIGS. 1-3. The catheter hub (102) includes a proximal end (134) and a distal end (136). It is to be understood that the term 'proximal end' as used in the present disclosure may be defined as an end closer to the operator who operates the catheter device (100). The term 'distal end' as used in the present disclosure may be defined as an end opposite to the 'proximal end' and away from the operator. In an embodiment, the catheter hub (102) can be made of a bio-compatible material which can be rigid and can securely hold components associated with it. The catheter hub (102) includes a catheter tube (138) (shown in FIGS. 1 and 2) fixedly connected at the distal end (136) of the catheter hub (102). The catheter tube (138) can be made of a flexible or a soft material, including, but not limited to, a plastic or a polymer or a bio-compatible material which is flexible/soft in nature. The catheter tube (138) is a thin elongated tubular structure having a bore (140). The bore (140) of the catheter tube (138) is adapted to encase the needle (116) of the intravenous catheter device (100). The catheter tube (138) can be adapted to fix with the catheter hub (102) by a method including, but not limited to, a press fitting or adhesive bonding or any other methods known in the art to serve a purpose of holding the catheter tube (138) with the catheter hub (102). In another embodiment, the catheter tube (138) may be manufactured integral with the catheter hub (102).

In the illustrated embodiment shown in FIGS. 1-4, the catheter hub (102) further includes an outer port (142) abutting on an outer surface (144) of the catheter hub (102) forming an auxiliary fluid pathway (146) in communication with a co-axial recess (148) of the catheter hub (102). Thus, the intravenous catheter device (100) in this embodiment is adapted to be having a two-way fluid mechanism. The outer port (142) of the catheter hub (102) may be provided with a dispensing cap (150) (shown in FIGS. 1 and 2) for opening and closing of the outer port (142) for supply of a fluid (not shown). The dispensing cap (150) may be operated to open and close via a hinge or threads or any other mechanism known in the art.

The catheter hub (102) further includes an annular stopper (152) on an inner surface (154) of the catheter hub (102). The annular stopper (152) is disposed at the proximal end (134) of the catheter hub (102). The co-axial recess (148) of the catheter hub (102) includes an undercut portion (156) (shown in FIGS. 3 and 8). In the illustrated embodiment, the undercut portion (156) is provided towards the distal end (136) of the catheter hub (102). In the illustrated embodiment, the luer lock cap (128) is provided to seal the proximal end (134) of the catheter hub (102). The catheter hub (102) is adapted to accommodate a valve member (158) of the catheter device (100).

In the illustrated FIGS. 1-3, the valve member (158) is adapted to be disposed inside the co-axial recess (148) of the catheter hub (102). The valve member (158) is defined by a cylindrical portion (160) (more clearly shown in FIG. 6a) and a curved portion (162) (more clearly shown in FIG. 6a) disposed at one end of the cylindrical portion (160). The cylindrical portion (160) of the valve member (158) has a protrusion (164) (shown in FIG. 6b) at an inner surface (166). The valve member (158) further includes a co-axial recess (168) (shown in FIG. 6b) extending from the cylindrical portion (160) to the curved portion (162). In the illustrated embodiment, the curved portion (162) is in convex shape, however, the curved portion (162) may also be other shapes such as but not limited to, a frusto-conical shape. The terms "curved portion" and "convex portion" as used in the present disclosure are interchangeably used, and they relate to same portion of the valve member (158). The convex portion (162) of the valve member (158) is provided with one or more slits (170), thereby defining a plurality of prongs (172). The one or more slits (170) are designed to allow the needle (116) to pass through the slits (170) so that the slits (170) can self-seal once the needle (116) is withdrawn.

In the illustrated embodiment, the valve member (158) is adapted to be held in place at the co-axial recess (148) of the catheter hub (102) when a first end (174) of the valve member (158) abuts the annular stopper (152) of the catheter hub (102). In an exemplary embodiment, the valve member (158) is made of a flexible material selected from a group consisting of silicone and rubber, where the slit (170) is of shape such as, but not limited to, 'Y' or inverted 'Y' or 'X', or a horizontal slit or a vertical slit or '+' shape or combination of the same or any other shape which will facilitate opening and expanding of the plurality of prongs (172) during the insertion of the needle (116) and an actuator member (176) respectively, inside the co-axial recess (168) of the valve member (158).

Figure 5A:
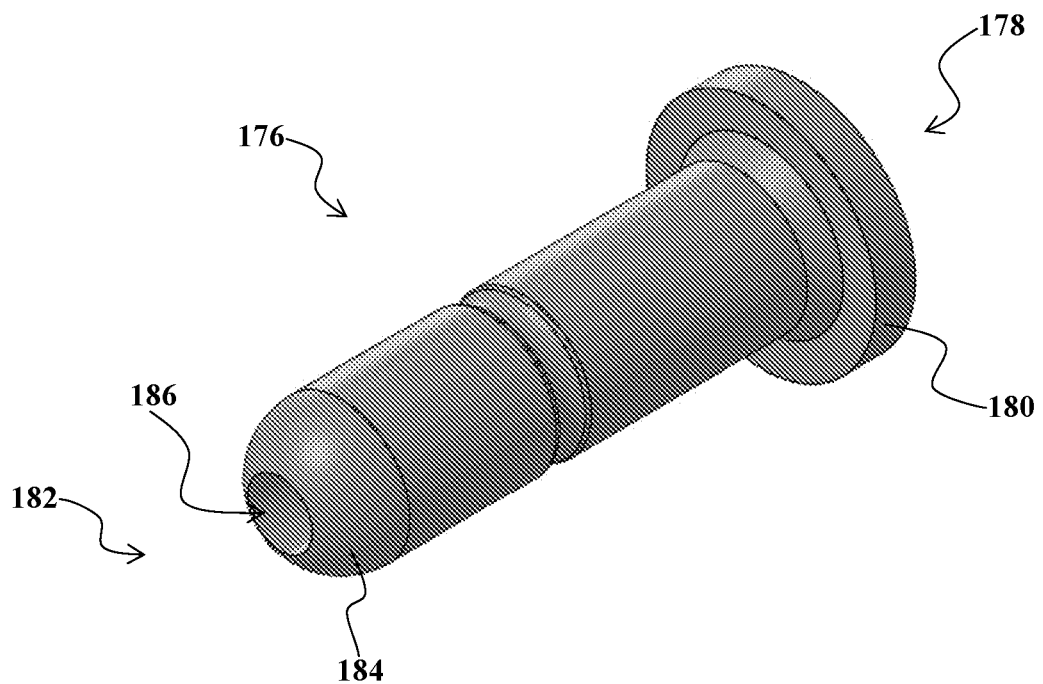
FIG. 5a and FIG. 5b shows a perspective view and a sectional view of an actuator member of the intravenous catheter device shown in FIGS. 1-4, according to an exemplary embodiment of the present disclosure.
Figure 5B:
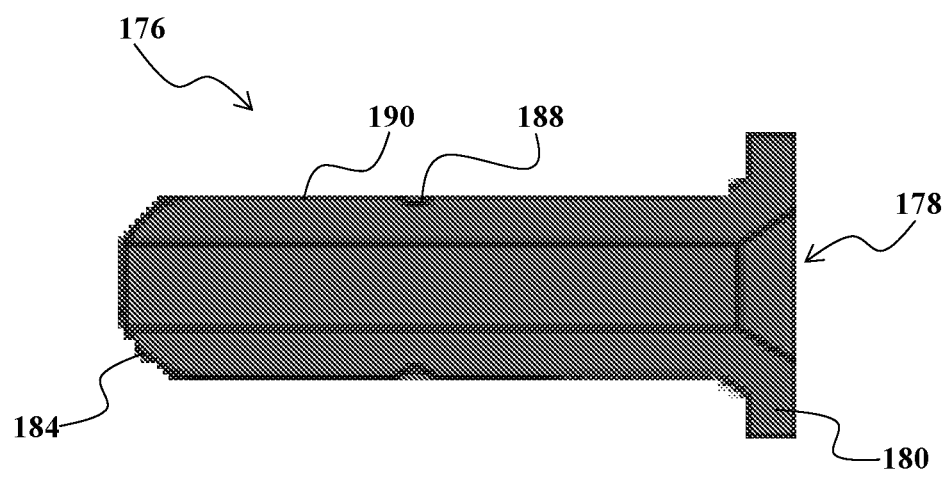
Figure 7A:
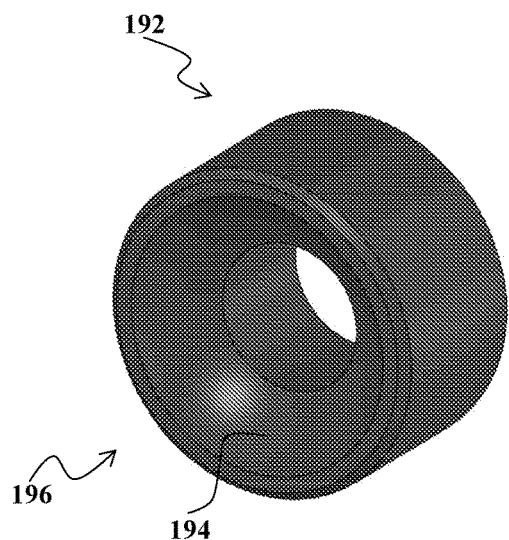
FIGS. 7a-7d shows a perspective view, a sectional view, a front view, and a rear view of a valve closure member of the intravenous catheter device shown in FIGS. 1-4, according to an exemplary embodiment of the present disclosure.
Figure 7B:
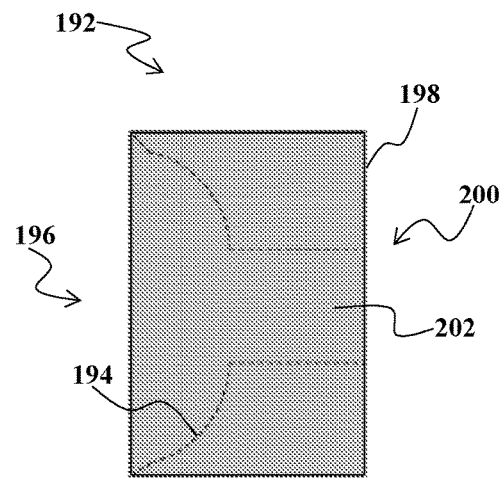
Figure 7C:
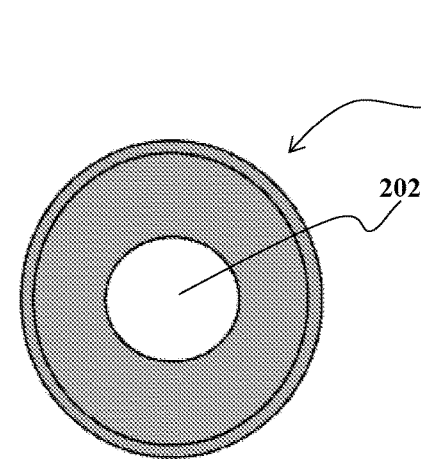
Figure 7D:
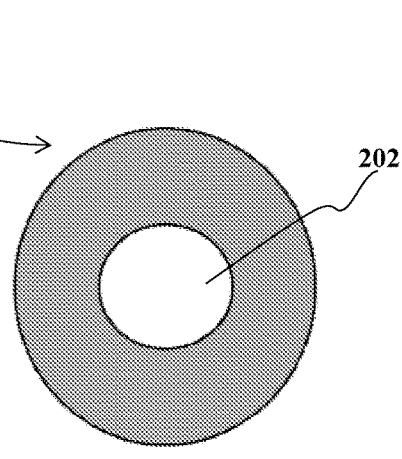

FIG. 5 illustrates a perspective view of the actuator member (176) of the intravenous catheter device (100) shown in FIGS. 1-4, according to an exemplary embodiment of the present disclosure. The actuator member (176) includes a first end (178) having a radially extending flange (180), a second end (182) having a convex surface (184) and an axial bore (186) between the first end (178) and the second end (182) of the actuator member (176). In an exemplary embodiment, the actuator member (176) is made of medical usage compatible material known in the art, such as, but not limited to, a rigid plastic material for example Polyoxymethylene (POM) or a metal for example Stainless Steel.

The actuator member (176) further includes a circular recess (188) on an outer surface (190). The protrusion (164) of the valve member (158) is adapted to engage with the circular recess (188) of the actuator member (176). The engagement of the protrusion (164) of the valve member (158) and the circular recess (188) of the actuator member (176) places an assembly of the valve member (158) and the actuator member (176) intact inside the catheter hub (102), such that the assembly of the valve member (158) and the actuator member (176) does not fall from the catheter hub (102). In another embodiment, the valve member (158) and the actuator member (176) may be connected by any other methods apart from the protrusion (164) and the recess (188), for example threads (not shown), or snap fit arrangement (not shown) etc., known in the art. In yet another embodiment, the actuator member (176) can include a protrusion similar to that of the protrusion (164) made on the valve member (158) and the valve member (158) may include a circular recess similar to that of the circular recess (188) of the actuator member (176). It should be understood that the circular recess (188) and the protrusion (164) made on the actuator member (176) and the valve member (158) should not be limiting the scope of the present disclosure, and any suitably mechanism (for example: threads) which serves the purpose of making the actuator member (176) and the valve member (158) unison may also be used.

FIGS. 7a to 7d illustrate various views of a valve closure member (192) of the intravenous catheter device (100) shown in FIGS. 1-4, according to an exemplary embodiment of the present disclosure. The valve closure member (192) includes a first surface (194) at a proximal end (196), a second surface (198) at a distal end (200) and a through hole (202) extending between the proximal end (196) and the distal end (200). The valve closure member (192) is disposed inside the catheter hub (102) such that the second surface (198) of the valve closure member (192) abuts the undercut portion (156) of the catheter hub (102) and the first surface (194) of the valve closure member (192) abuts the convex portion (162) of the valve member (158).

In the illustrated embodiment, the convex portion (162) of the valve member (158) conforms to a shape of the first surface (194) of the valve closure member (192). In an embodiment, the valve closure member (192) has a hardness ranging from about 50 shore to 80 shore and the valve member (158) has hardness ranging from about 20 shore to 45 shore.

Figure 8:
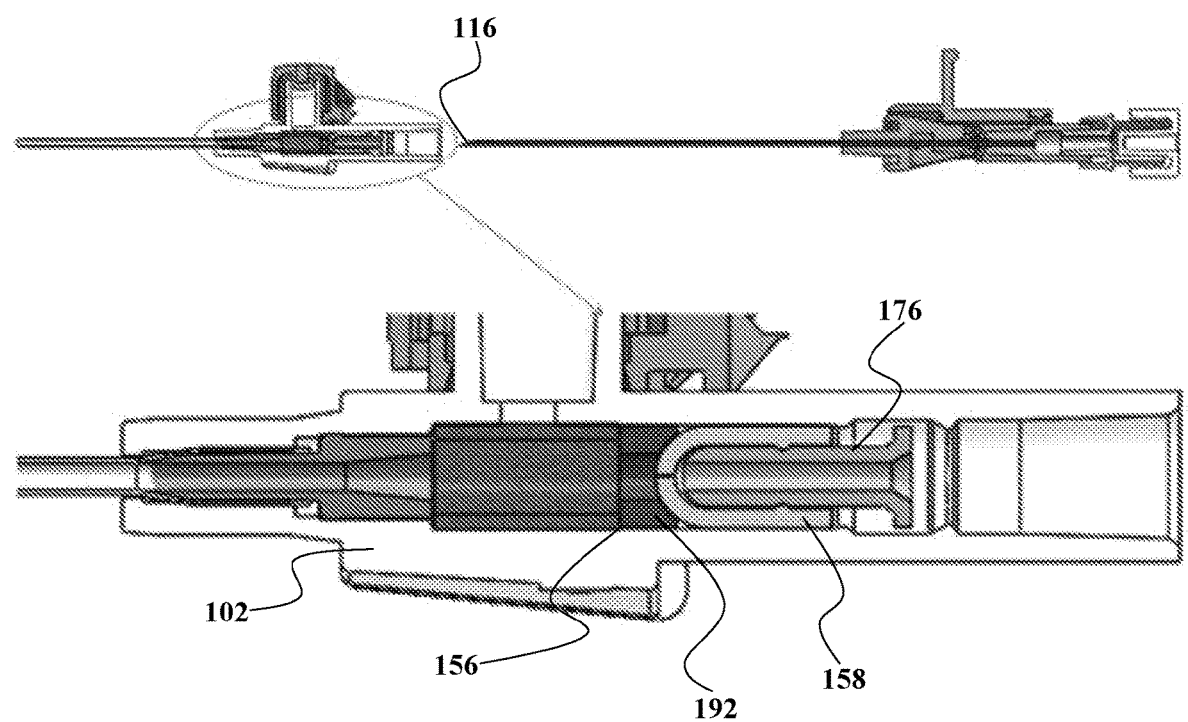
FIG. 8 shows sectional views the intravenous catheter device showing operation of the intravenous catheter device when needle is inserted into the valve member for puncturing a vein, according to an exemplary embodiment of the present disclosure.

FIG. 8 illustrate sectional views the intravenous catheter device (100) showing an operation of the intravenous catheter device (100) for vein puncturing, according to an exemplary embodiment of the present disclosure. When the needle (116) is passed through the co-axial recess (148) of the catheter hub (102) and via the actuator member (176), the needle (116) is adapted to pierce through the slits (170) of the valve member (158). After piercing the slits (170) of the valve member (158), the needle (116) passes through the catheter tube (138) for puncturing the vein of the patient.

When the needle (116) is withdrawn after puncturing the vein, the slits (170) of the valve member (158) will close itself since the valve member (158) is made of flexible material which can self-close the opening at the slits (170) of the convex portion (162) of the valve member (158).

In an embodiment, the catheter device (100) can include a needle stick safety device (not shown), known in the art. The needle stick safety device can be adapted to accommodate the tip of the needle (116) to reside within the needle cover (104). In an embodiment, the needle stick safety device may include a spring retainer (not shown) holding an enlarged dimension portion (not shown) of the needle (116) thereby preventing exposure of the tip of the needle (116) outside the needle cover (104) to prevent needle stick injury to the operator or to the patient.

Figure 9:
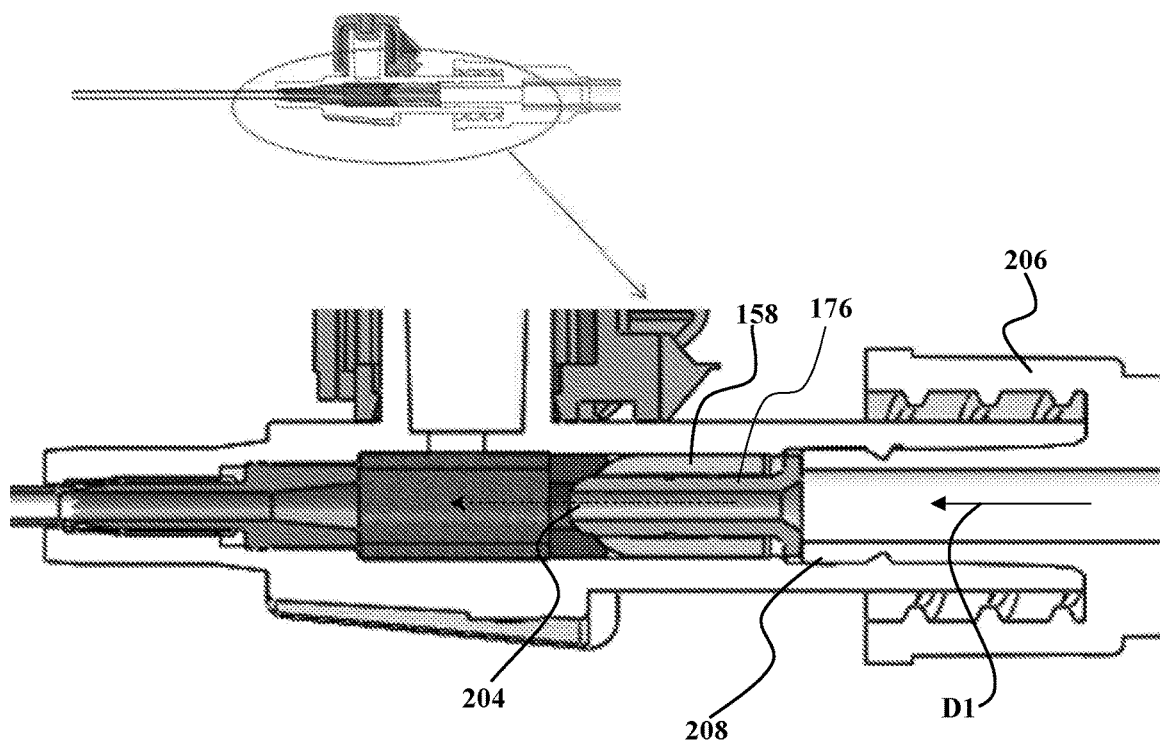
FIG. 9 shows sectional views the intravenous catheter device showing operation of a luer lock member for creating passage for fluid flow, when the luer lock member is releasably connected to a proximal end of the intravenous catheter device, according to an exemplary embodiment of the present disclosure.

FIG. 9 illustrate sectional views the intravenous catheter device (100) showing working of the catheter device (100) for creating a passage (204) for fluid flow when a luer lock member (206) is releasably connected to the catheter device (100), according to an embodiment of the present disclosure.

In the illustrated embodiment, the luer lock member (206) is releasably connected at a proximal end (134) of the catheter hub (102) via means known in the art such as, but not limited to, 6% universal taper. The luer lock member having 6% universal taper should not be meant to be limiting the scope of the present disclosure. Any luer lock member of standard size or having the ISO standards which conforms with the fitment part of the catheter device (100) can be used. For example, the ISO standards ISO-80369-20 and ISO-80369-7 can be used for luer lock member having 6% universal taper.

In another embodiment (not shown) the luer lock member (206) may have any of the various configurations or shapes available from various suppliers or manufacturers. One such shape may be a luer slip instead of a luer lock. The functioning of the device will remain unchanged as long as the luer lock or luer slip follows a 6% taper.

The engagement of luer lock member (206) at the proximal end (134) of the catheter hub (102) generates a force on the actuator member (176) along an axis (X-X') of the catheter hub (102) and towards the distal end (136) of the catheter hub (102). That is to say, when a front end (208) of the luer lock member (206) is adapted to contact the flange (180) of the actuator member (176), the actuator member (176) is displaced axially in a direction "D1" towards the distal end (136) of the catheter hub (102). The axial displacement of the actuator member (176) towards the distal end (136) of the catheter hub (102) opens the plurality of prongs (172) of the valve member (158) to form the passage (204) for the fluid flow from the proximal end (134) of the catheter hub (102) to the distal end (136) of the catheter hub (102).

Figure 10:
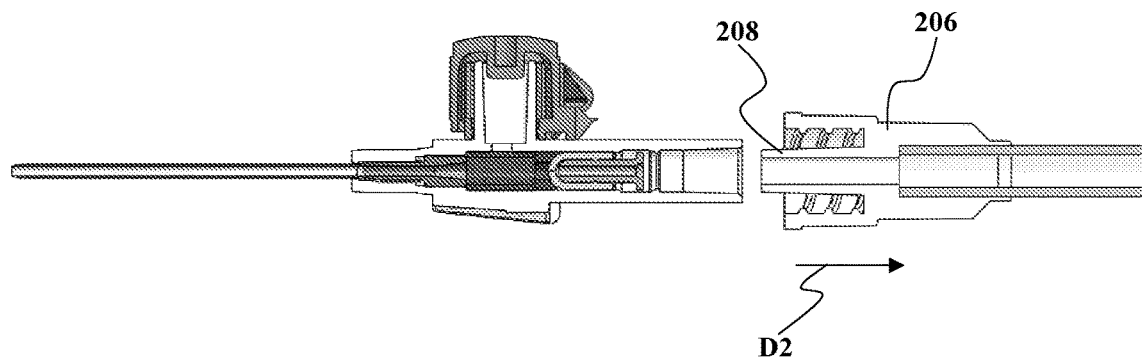
FIG. 10 shows a sectional view of the intravenous catheter device shown in FIG. 9, when the luer lock member is in disengaged position and when the passage for the fluid flow is closed, according to an exemplary embodiment of the present disclosure.
Figure 11:
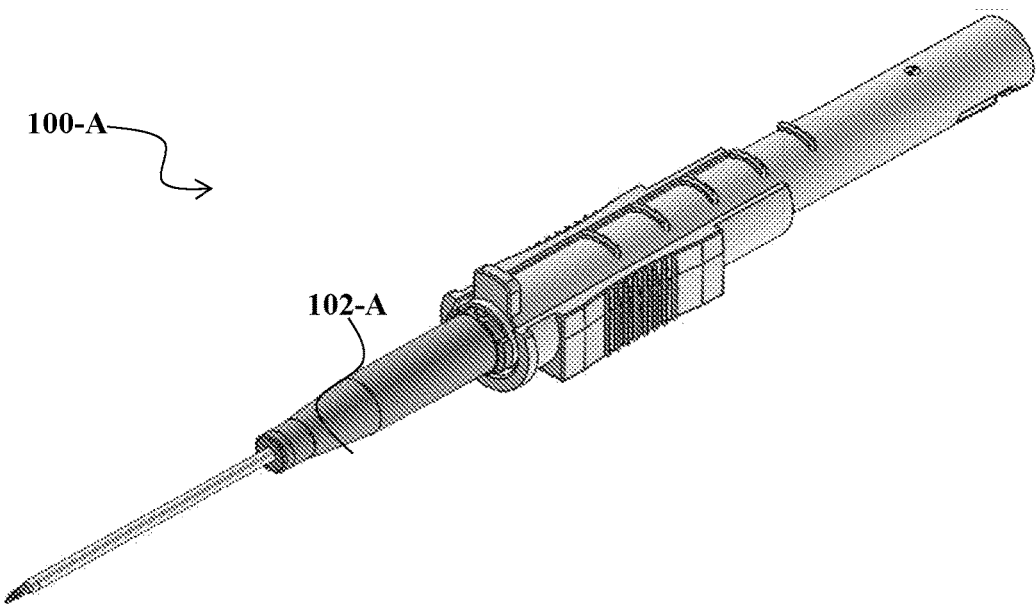
FIGS. 11 and 12 shows a perspective view and a sectional view of an intravenous catheter device according to another exemplary embodiment of the present disclosure.
Figure 12:
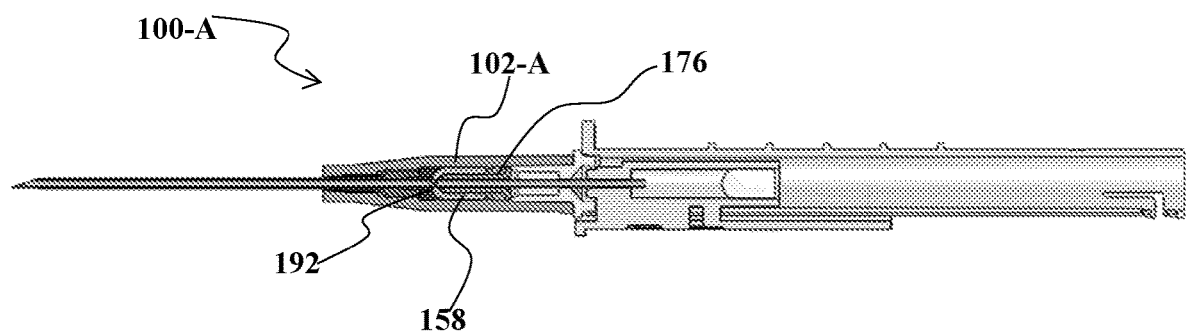

FIG. 10 illustrates a sectional view of the intravenous catheter device (100) shown in FIG. 9 when the luer lock member (206) is in disengaged position. When the luer lock member (206) is disengaged from the catheter hub (102), the valve closure member (192) in the catheter device (100) is adapted to close the plurality of prongs (172) of the valve member (158), thereby closing the passage (204) for the fluid flow and preventing blood flow from the punctured vein of the patient from the distal end (136) of the catheter hub (102) to the proximal end (134) of the catheter hub (102).

This is due to the fact that the valve closure member (192) has a hardness greater that the hardness of the plurality of prongs (172) of the valve member (158), and when the luer lock member (206) is disengaged from the catheter hub (102), the valve closure member (192) pushes the plurality of prongs (172) of the valve member (158) and the actuator member (176) in a direction "D2" away from the distal end (136) of the catheter hub (102), thereby closing the passage (204) for the fluid flow and preventing blood flow from the punctured vein of the patient from the distal end (136) of the catheter hub (102) to the proximal end (134) of the catheter hub (102).

Advantages:

The disclosed valve closure member (192) when pushes or closes the plurality of prongs (172) of the intravenous catheter device (100), an undesired reverse flow of blood from the vein of the patient is prevented when the actuator member (176) is displaced due to removal of the luer lock member (206).

The disclosed valve closure member (192) and the actuator member (176) may be activated or de-activated multiple times to allow flow of blood through the needle when vein of the patient is punctured or to prevent undesired reverse flow of blood, with the efficacy of such flow/prevention of flow being similar in each activation or deactivation.

The disclosed plurality of prongs (172) of the valve member (158) being flexible when compared with the hardness of the valve closure member (192), the plurality of prongs (172) will close the slit (170) by folding back by themselves automatically when the needle (116) is withdrawn after puncturing of the vein is prevented.

The disclosed intravenous catheter device (100) prevents contact of blood of the patient to a user's hands since the reverse flow of the blood is prevented due to closing of the plurality of prongs (172) of the valve member (158) by the valve closure member (192). Thereby, preventing the infections and deceases that may be caused due to the blood contact.

The disclosed intravenous catheter device (100) is economical since the assembly of the valve member (158), the actuator member (176) and the valve closure member (192) are made of plastic or bio-compatible material.

The disclosed intravenous catheter device (100) provides an improved closing of the slits (170) of the valve member (158) since the plurality of prongs (172) of the valve member (158) is closed due to the pushing force acting towards the proximal end (134) of the catheter hub (102) of the user or operator by the valve closure member (192), thereby closing the passage (204) without allowing reverse flow of blood.

Figure 13:
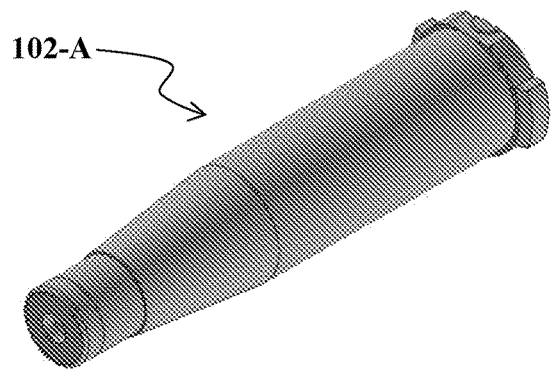
FIG. 13 shows a perspective view of a catheter hub of the intravenous catheter device shown in FIGS. 11 and 12.
Figure 14:
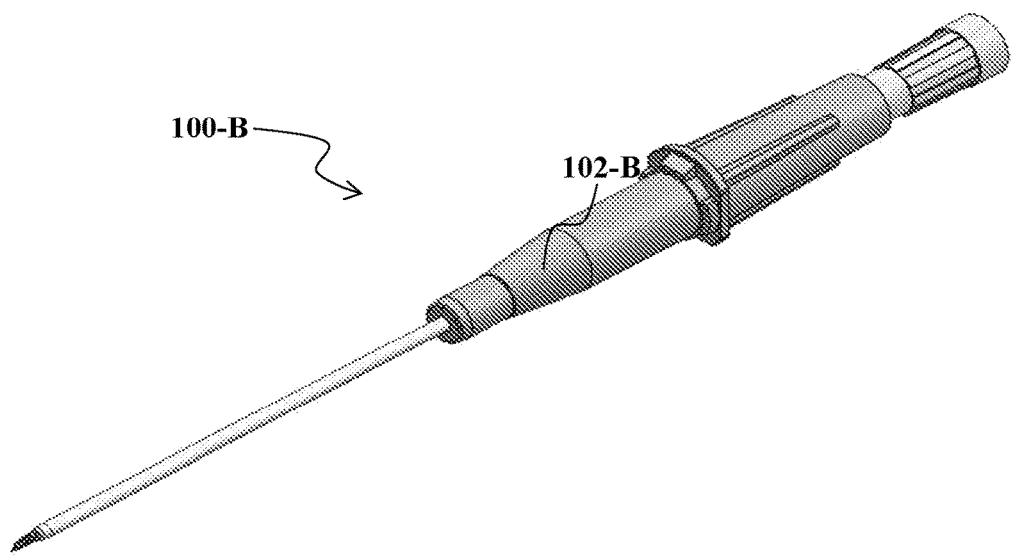
FIG. 14 shows a perspective view of an intravenous catheter device according to yet another exemplary embodiment of the present disclosure.
Figure 15:
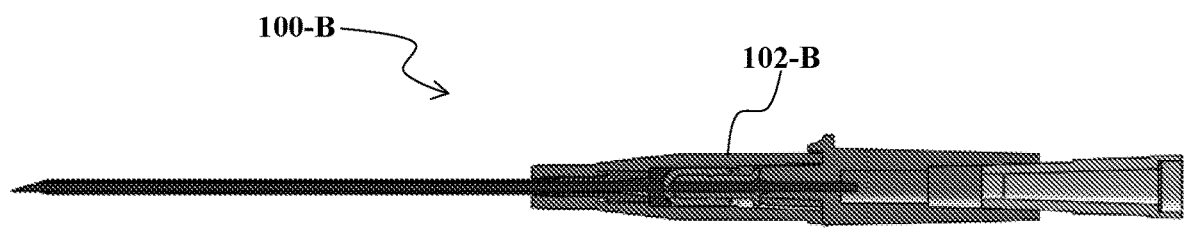
FIG. 15 shows a sectional view of the intravenous catheter device shown in FIG. 14.
Figure 16:
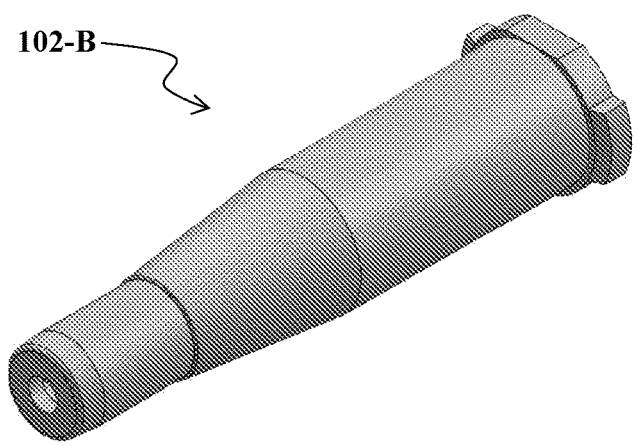
FIG. 16 shows a perspective view of a catheter hub of the intravenous catheter device shown in FIGS. 14 and 15.
Figure 17:
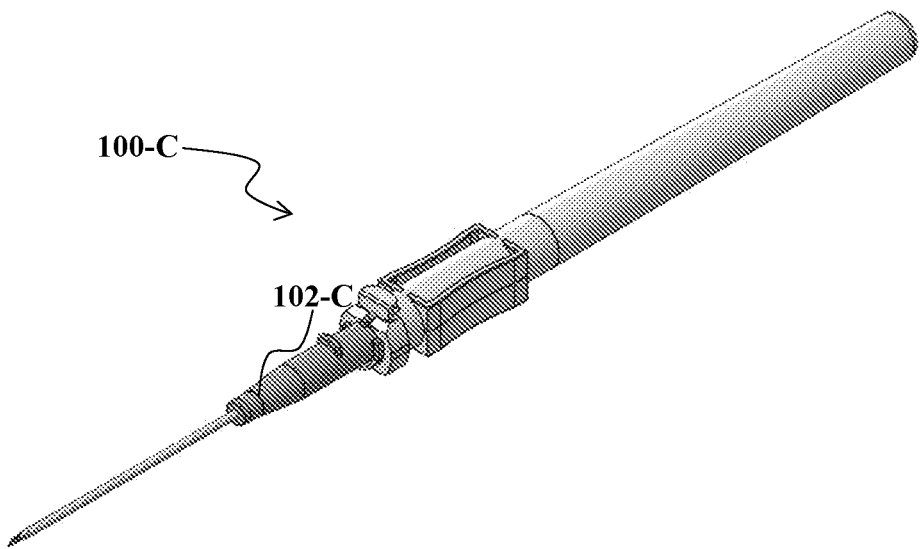
FIG. 17 shows a perspective view of an intravenous catheter device according to still another exemplary embodiment of the present disclosure.
Figure 18:
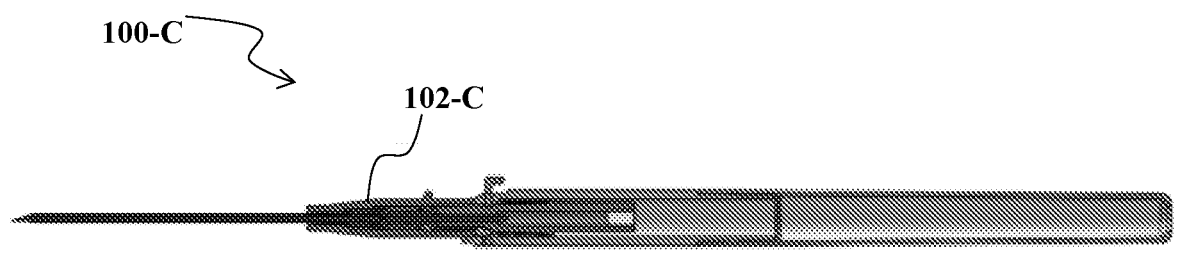
FIG. 18 shows a sectional view of the intravenous catheter device shown in FIG. 17.
Figure 19:
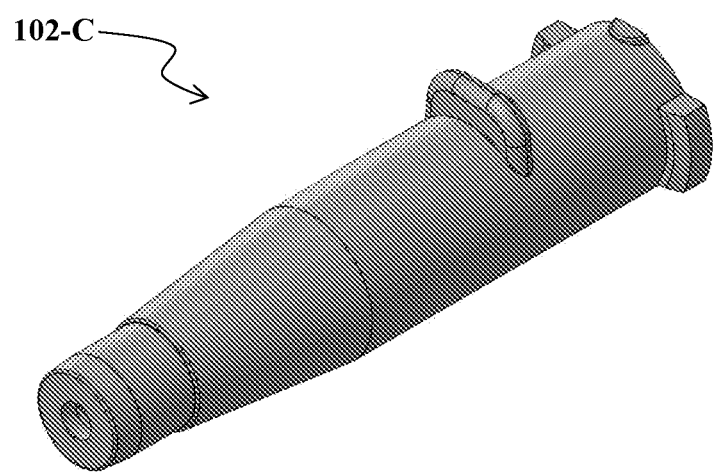
FIG. 19 shows a perspective view of a catheter hub of the intravenous catheter device shown in FIGS. 17 and 18.

Industrial Applicability:

The disclosed assembly of the valve member (158), the actuator member (176) and the valve closure member (192) can be used in one or more types of the catheter hubs (102-A, 102-B, 102-C) shown in FIG. 13, FIG. 16 and FIG. 19. The catheter hubs (102-A, 102-B, 102-C) disclosed in the FIG. 13, FIG. 16 and FIG. 19, are respectively used in catheter devices (100-A, 100-B, 100-C) shown in FIGS. 11, 12, 14, 15, 17 and 18. Therefore, application of the assembly of the valve member (158), the actuator member (176) and the valve closure member (192) are not meant to be limited to the intravenous catheter device (100) having the catheter hub (102) as disclosed in FIGS. 1-4.

The disclosed valve closure member (192) may find its application in other suitable medical devices where the requirement of prevention of reverse flow of blood or medicinal fluid is required.

While aspects of the present invention have been particularly shown and described with reference to the embodiments above, it will be understood by those skilled in the art that various additional embodiments may be contemplated by modification of the disclosed device without departing from the scope of what is disclosed. Such embodiments should be understood to fall within the scope of the present invention as determined based upon claims and any equivalents thereof.

LIST OF REFERENCE NUMERALS AND CHARACTERS

100: Catheter device or intravenous catheter device
100-A: Catheter device of another embodiment
100-B: Catheter device of yet another embodiment
100-C: Catheter device of still another embodiment
102: Catheter hub
102-A: Catheter hub of another embodiment
102-B: Catheter hub of yet another embodiment
102-C: Catheter hub of still another embodiment
104: Needle cover
106: Recess of the needle cover
108: Projection of the catheter hub
110: Tubular sleeve 112: Slit of the tubular sleeve
114: Bore of the tubular sleeve
116: Needle
118: Casing
120: Needle hub
122: Thumb grip
124: Flashback chamber
126: Extended portion of the flashback chamber
128: Luer lock cap
130: Porous filter
132: Hydrophobic filter
134: Proximal end of the catheter hub
136: Distal end of the catheter hub
138: Catheter tube
140: Bore of the catheter tube
142: Outer port
144: Outer surface of the catheter hub
146: Auxiliary fluid pathway
148: Co-axial recess of the catheter hub
150: Dispensing cap
152: Annular stopper
154: Inner surface of catheter hub
156: Undercut portion of the catheter hub
158: Valve member
160: Cylindrical portion of the valve member
162: Curved portion or convex portion of the valve member
164: Protrusion on an inner surface of the cylindrical portion
166: Inner surface of the cylindrical portion
168: Co-axial recess of the valve member
170: One or more slits
172: Plurality of prongs
174: First end of the valve member
176: Actuator member
178: First end of the actuator member
180: Radially extending flange of the actuator member
182: Second end of the actuator member
184: Convex surface
186: Axial bore of the actuator member
188: Circular recess of the actuator member
190: Outer surface of the actuator member
192: Valve closure member
194: First surface of the valve closure member
196: Proximal end of the valve closure member
198: Second surface
200: Distal end of the valve closure member
202: Through hole of the valve closure member
204: Passage for the fluid flow
206: Luer lock member
208: Front end of the luer lock member
A: Magnified portion
D1: Direction
D2: Direction
X-X': Axis of the catheter hub

I claim:

1. An intravenous catheter device comprising:
a catheter hub having a proximal end and a distal end, a co-axial recess with an annular stopper disposed at the proximal end of the catheter hub, and an undercut portion provided towards the distal end of the catheter hub;
a valve member being adapted to be disposed inside the co-axial recess of the catheter hub, the valve member being defined by a cylindrical portion, a co-axial recess extending from the cylindrical portion to a curved portion, the curved portion being provided with one or more slits defining a plurality of prongs, wherein the one or more slits are configured to allow a needle to pass through the one or more slits to puncture a vein of a patient;
a flashback chamber adapted to be disposed at the proximal end of the catheter hub, wherein a blood flow into the flashback chamber confirms puncturing of the vein by the needle;
an actuator member having an axial bore and a first, proximal end having a radially extending flange, the actuator member being adapted to be disposed within the co-axial recess of the valve member, wherein the actuator member is being displaced axially in a direction towards the distal end of the catheter hub thereby opening the plurality of prongs of the valve member to form a passage for a fluid flow from the proximal end of the catheter hub to the distal end of the catheter hub, when a luer lock member is removably connected at the proximal end of the catheter hub abutting the radially extending flange of the actuator member; and
a valve closure member comprising a first surface at a proximal end, a second surface at a distal end, and a through hole extending between the proximal end of the valve closure member and the distal end of the valve closure member, wherein the first surface of the valve closure member has a concave shape defining a cavity, the valve closure member being disposed inside the catheter hub such that the second surface of the valve closure member abuts the undercut portion of the catheter hub and the first surface of the valve closure member abuts the curved portion of the valve member,
wherein the valve closure member is adapted to close the plurality of prongs of the valve member, thereby closing the passage for the fluid flow and preventing blood flow from the punctured vein of the patient from the distal end of the catheter hub to the proximal end of the catheter hub when the luer lock member abutting the actuator member is removed.

2. The intravenous catheter device as claimed in claim 1, wherein the valve closure member has a hardness ranging from about 50 shore to about 80 shore and the valve member has a hardness ranging from about 20 shore to about 45 shore.

3. The intravenous catheter device as claimed in claim 1, wherein the curved portion of the valve member is in a convex shape or a frusto-conical shape.

4. The intravenous catheter device as claimed in claim 1, wherein the valve member is adapted to be held in place at the co-axial recess of the catheter hub when a first end of the valve member abuts the annular stopper of the catheter hub.

5. The intravenous catheter device as claimed in claim 1, wherein the valve member is made of a flexible material selected from a group consisting of silicone and rubber.

6. The intravenous catheter device as claimed in claim 1, wherein the one or more slits are of a Y-shape or an X-shape or a +shape or a combination of the same.

7. The intravenous catheter device as claimed in claim 1, wherein the cylindrical portion of the valve member has a protrusion at an inner surface.

8. The intravenous catheter device as claimed in claim 7, wherein the actuator member has a circular recess at an outer surface of the actuator member, and wherein the protrusion of the valve member is adapted to engage with the circular recess of the actuator member, thereby to place an assembly of the valve member and the actuator member intact inside the catheter hub.

9. The intravenous catheter device as claimed in claim 1, wherein the actuator member includes a first end having a radially extending flange and a second end having a convex surface, wherein the axial bore is between the first end and the second end of the actuator member.

10. The intravenous catheter device as claimed in claim 1, wherein the valve closure member is harder than the plurality of prongs of the valve member, wherein when the luer lock member is disengaged from the catheter hub, the valve closure member pushes the plurality of prongs and the actuator member in a direction away from the distal end of the catheter hub thereby closing the passage for the fluid flow and preventing blood flow from the punctured vein of the patient from the distal end of the catheter hub to the proximal end of the catheter hub.

11. The intravenous catheter device as claimed in claim 1, wherein the actuator member is made of a rigid plastic material or a metal.

12. The intravenous catheter device as claimed in claim 1, wherein the flashback chamber includes any one of a porous filter and a cover to allow air to escape and blood to flow inside the flashback chamber.

13. The intravenous catheter device as claimed in claim 1, further comprising a needle stick safety device.

14. The intravenous catheter device as claimed in claim 1, wherein the perimeter of the radially extending flange protrudes away from a cylindrical outer surface of the actuator member.

15. The intravenous catheter device as claimed in claim 1, wherein the axial bore comprises an enclosed lumen extending longitudinally through the actuator member from the first, proximal end of the actuator member to a distal end of the actuator member.

* * * * *